United States Patent [19]

Wang

[11] Patent Number: 4,794,379
[45] Date of Patent: Dec. 27, 1988

[54] AUTOMATIC ALARM DEVICE FOR DRIPPING INJECTION FLUID BOTTLE

[75] Inventor: Kuo-Hsien Wang, Keelung, Taiwan

[73] Assignee: Tech Zeal Industrial Company Ltd., Taiwan

[21] Appl. No.: 10,405

[22] Filed: Feb. 3, 1987

[51] Int. Cl.⁴ ............................................. G08B 21/00
[52] U.S. Cl. ............................ 340/624; 128/DIG. 13; 340/693
[58] Field of Search ............... 128/DIG. 13; 604/127, 604/254; 340/623, 624, 618, 693; 222/67

[56] References Cited

U.S. PATENT DOCUMENTS

| | | | |
|---|---|---|---|
| 2,684,414 | 7/1954 | Kilpatrick | 340/623 X |
| 2,850,211 | 9/1958 | Fernandez | 604/127 X |
| 3,942,526 | 3/1976 | Wilder et al. | 604/253 |
| 4,244,364 | 1/1981 | Grushkin | 340/324 X |

*Primary Examiner*—Herbert Goldstein
*Assistant Examiner*—Jeffery A. Hofsass
*Attorney, Agent, or Firm*—Ostrolenk, Faber, Gerb & Soffen

[57] ABSTRACT

An automatic alarm device for dripping injection fluid bottle, which is installed in the bottle neck portion, and it comprises of a case body, a buoyant power switching device, a buzzer, and a flashing device. The buoyancy of injection fluid pulls a buoy, which is immersed in the injection fluid, upwardly, then the lower end of the buoy connecting rod is lifted up against a extension coil spring, thereby, the electric connection between contacts of power switching device is broken (power OFF position) by leaf spring force of the top contact of the power switching device; when the injection fluid in the bottle is almost completely utilized to a certain level, the buoy losts its buoyancy, and the extension coil spring pulls the lower end of the buoy connecting rod downwardly to push the top contact to be connected electrically to the button contact of the power switching device (power "ON" position), at this time, the power is ON and the buzzer will start to flash to alert the nurse or doctor to take immediate action for the patient.

6 Claims, 2 Drawing Sheets

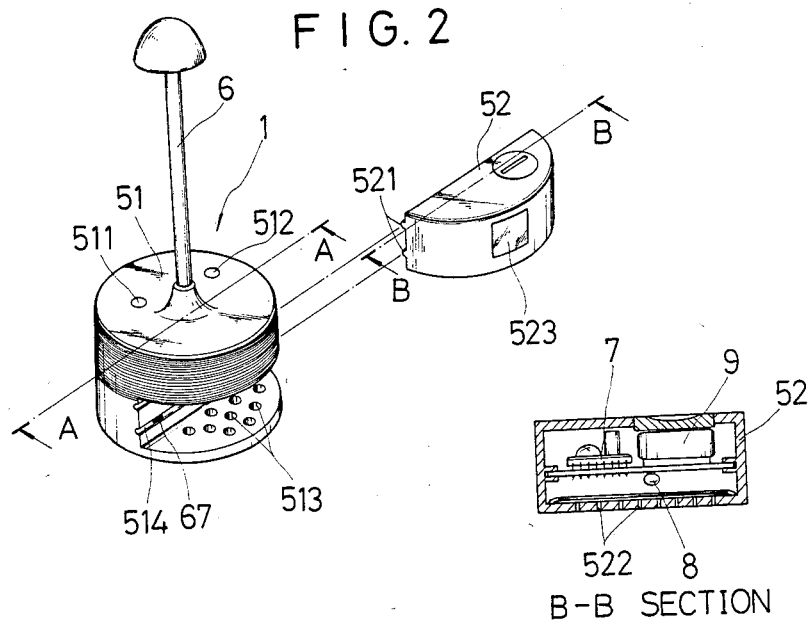
FIG. 2
B-B SECTION
FIG. 4
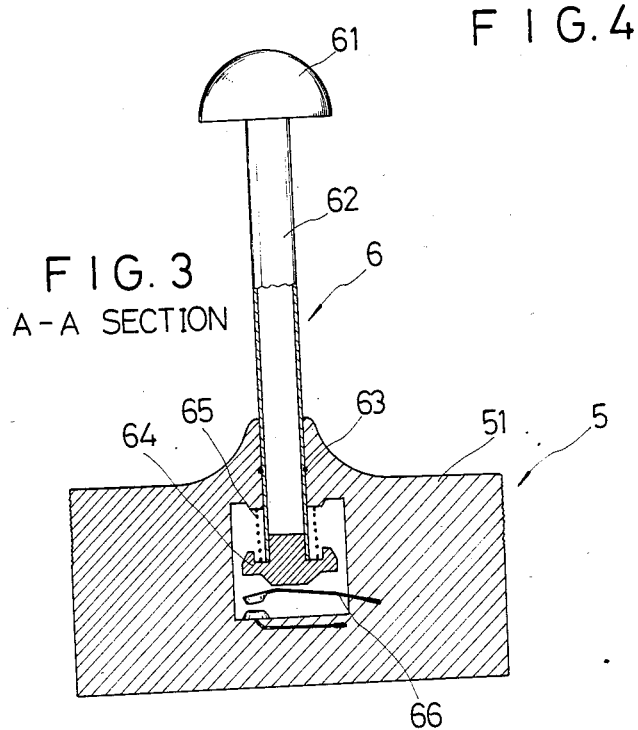
FIG. 3
A-A SECTION

4,794,379

AUTOMATIC ALARM DEVICE FOR DRIPPING INJECTION FLUID BOTTLE

FIELD OF THE INVENTION

The invention is related to an automatic alarm device for dripping injection fluid bottle, especially the medical dripping injection fluid. When the whole bottled fluid has been used to a predetermined level but before becoming empty, alarm devices will be actuated to alert a nurse or doctor to take immedaite actions for the patient.

BACKGROUND OF THE INVENTION

Nowadays, dripping injection medical technique is widely utilized in every hospital. Dripping injection to be done frequently requires several hours. In addition, there are large numbers of sick cases need dripping injection care. Therefore, after the dripping injection device has been connected to a patient, the medical personnel leave this patient alone and go out to see another patient, and only occasionally come to watch the status of their patients. As to patients, they frequently have psychological burden and feel uneasy or afraid that air may to into their blood vessel when dripping injection fluid is completely used up without medical personnel to take care of it. Therefore, they can't sleep, even feel very tired. They still open their eyes to watch the status of injection fluid.

OBJECTS OF THE INVENTION

The objects of the invention are to resolve the above said shortcomings, and to provide an automatic alarm device for dripping injection fluid Bottle, when the fluid in the dripping injection fluid bottle is almost used up, an alarm buzzer will buzz and an alarm flashing device will flash to alert medical personnel to take immediate action for the patient. In this way, the psychological burden of the patients is removed, the patients can go sleep without any fear about their dripping injection time period.

SUMMARY OF THE INVENTION

An automatic alarm device for dripping injection fluid bottle is installed in the bottle neck portion of a dripping injection fluid bottle. During utilization the bottle is inverted upside down with the bottle neck portion facing downward. The buoyancy of fluid in the bottle pulls a buoy, which is immersed in the fluid, upwardly and causes the lower end of the buoy connecting rod to move upwardly against a coil extension spring. When fluid in the dripping injection fluid bottle is almost used up to a predetermined level, no more fluid buoyancy acts on the buoy, and the lower end of buoy connecting rod is lowered down by both coil extension spring force and gravitational force. A power switching device is actuated to "ON" position, and causes the buzzer to buzz and the flashing device to flash to alert medical pesonnel to take immediate action for the patient.

BRIEF DESCRIPTION OF THE DRAWINGS

FIG. 2 shows a perspective view of the invention.
FIG. 3 shows the sectional view at line A—A of FIG. 2.
FIG. 4 shows the sectional view at line B—B of FIG. 2.

SPECIFIC DESCRIPTION

Figure 1:
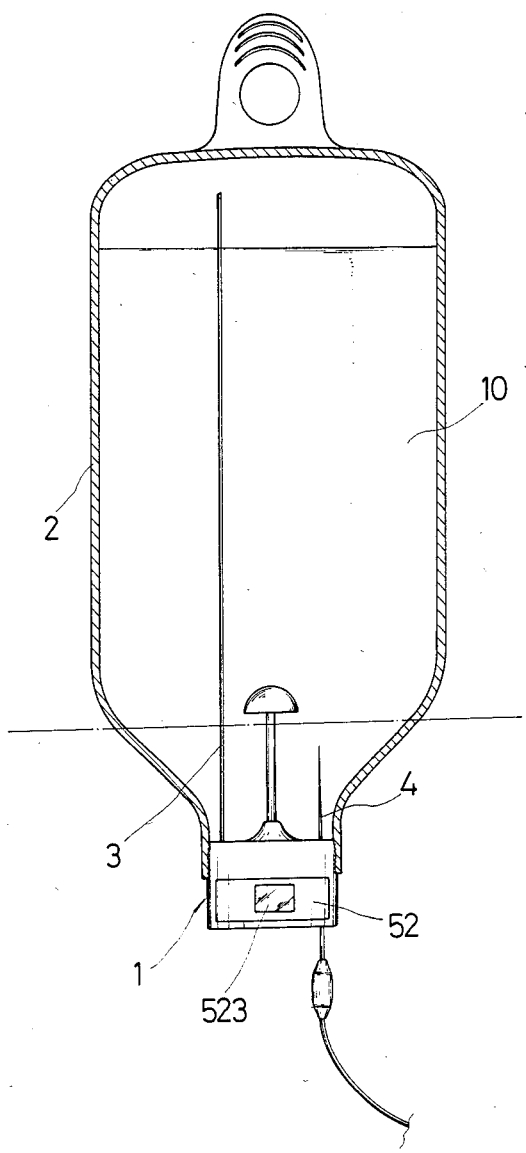
FIG. 1 shows a view of the invention which has been installed into a dripping injection fluid bottle.

As shown in FIG. 1, the utilization of the invention is similar to a traditional one. The alarm device 1 is plugged into the bottle neck portion of a dripping injection fluid bottle 2, the air inlet tube 3 and injection fluid tube 4 are installed on the alarm device 1.

As shown in FIGS. 2, 3, and 4, the alarm device 1 of the invention comprises a case body 5, a buoyancy actuated power switching device 6, a buzzer 7, a flashing device 8. Case body 5 (as shown in FIG. 2) comprises of a main body 51, and a clipping-on body 52. The main body 51 is provided with a buoyancy actuated power switching device 6, two openings 511, 512 for insertion of air inlet tube 3 and injection fluid slots 514. The clipping-on slots 514 are provided with power supply contact point 67 of buoyancy actuated power switching device 6. When clipping-on body 52 is clipped on the main body 51, the contact point of dovetail 521 will be connected to power supply contact point 67. The clipping-on body 52 is a small semicircular box, which contains a buzzer 7, a flashing device 8, and a battery 9 to power the buzzer and flashing device (as shown in FIG. 4). Also it is provided with sound holes 522 and a flash window 523. The buoyancy actuated power switching device 6 (as shown in FIG. 3) is located in the main body 51 of case body 5, which comprises a buoy 61, a buoy connecting rod 62, a sealing ring 63, an end piece 64, a coil extension spring 65, a pressure sensitive switch 66, and a power supply contact point 67. The buoy 61 and buoy connecting rod 62 can be an integrated part or two independent parts to be connected together. The buoy is a hollow body. It possesses buoyancy when it is immersed into the injection fluid. The lower portion of buoy connecting rod 62 is provided with an encircling slot for the reception of sealing ring 63 to prevent injection fluid from coming in. Also the lower portion of the buoy connecting rod is fitted with a coil extension spring 65, and the lower end of the coil extension spring 65 is seated on the end piece 64 for positioning. Below the end piece 64, is provided a pressure sensitive switch 66, and this switch is connected to power supply contact point 67 of clipping-on slot 514 by a conductor.

The principle of operation of the invention is based on buoyancy of injection fluid 10 of the injection bottle 2, which pulls the buoy 61 and buoy connecting rod 62 upwardly against coil extension spring 65 force. This causes the pressure sensitive switch to stay in "OFF" position for normal dripping injection. When the injection fluid 10 in the dripping injection fluid bottle 2 is almost used up to a predetermined level, the buoy 61 will lose its buoyancy, and the coil extension spring 65 pushes the end piece 64 down to actuate the pressure sensitive switch 66 to its "ON" position. The electric circuit in clipping-on body 52 is completed, at this time, the buzzer will buzz and the flashing device will flash to alert medical personnel to take immediate actions for the patient.

I claim:
1. An alarm for an intravenous liquid injection bottle:
said alarm having a casing and means for sealing said casing in a bottle;
means for permitting fluid from the bottle to flow through said casing;

a buoyant member supported on said casing in the bottle projecting above said casing and disposed in the path of fluid flow;

an end member in said casing and attached to said buoyant member to move with said buoyant member; said buoyant member moving in one direction with respect to said casing in response to the fluid level in said casing and moving said end member correspondingly;

a compression spring between said end member and said casing for moving said end member and said buoyant member counter to the buoyant motion thereof which responds to fluid level;

a switch in said casing positioned for being engaged by said end member when said end member is moved by said compression spring which occurs when the fluid in said casing approaches exhaustion and declines below the level of said buoyant member; upon being engaged, said switch being movable to a switch closed position;

a power source and an alarm in said casing in circuit with said switch for being connected together for activating said alarm when said switch is in said closed position.

2. An automatic alarm for a drip type of injection fluid bottle, the bottle having a bottleneck;

said automatic alarm having a casing, said casing being shaped for being sealed in the bottleneck;

said automatic alarm casing supporting a buoyancy responsive power supply switch, said casing having in it an alarm and a power supply for operating said alarm;

said power supply switch including:

a hollow buoy shaped for extending and extending above said casing; and a connecting rod for said buoy extending into said casing, said rod being sealed where it enters said casing to prevent injection fluid from entering said casing; said buoy being buoyant when immersed in the injection fluid in the bottle;

an end piece of said rod in said casing;

a power supply contact point disposed below said end piece;

a coil extension spring connected between said end piece of said buoy and said casing for driving said buoy and said rod counter to their motion caused by the buoyancy;

and an electrical conductor from said power supply through said switch to said alarm;

means in said casing connected to said switch to drive said switch to the switch ON position;

the buoyancy of said buoy driving said buoy to move away from said switch permitting said switch to remain in OFF position;

when the fluid level reduces and is used up, the buoyancy of said buoy is reduced driving said end piece under the influence of said spring to move said switch to the switch ON position and actuating said alarm.

3. The automatic alarm of claim 2, in which said alarm is an electric alarm comprising a flashing light.

4. The automatic alarm of claim 2, wherein said alarm is a sonic alarm.

5. The automatic alarm of claim 2, wherein said power source is an electric battery.

6. The automatic alarm of claim 2, wherein the casing is in two separable parts held together to define the casing, with the buoyant member, rod and end piece in one part and said switch, alarm and power source in the other part.

* * * * *